US006290944B1

(12) United States Patent
Garnier et al.

(10) Patent No.: US 6,290,944 B1
(45) Date of Patent: Sep. 18, 2001

(54) DETERGENT COMPOSITIONS CONTAINING AN HYDROXYLALKYL ETHER SURFACTANT AND A CATIONIC GUAR GUM

(75) Inventors: Nathalie Garnier, Springfield, NJ (US); Danièle Cauwet-Martin, Paris; Serge Restle, Saint-Prix, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/504,620

(22) Filed: Feb. 15, 2000

(30) Foreign Application Priority Data

Feb. 16, 1999 (FR) .................................................. 99 01867

(51) Int. Cl.$^7$ .................................................. A61K 7/075
(52) U.S. Cl. ................. 424/70.21; 424/70.1; 424/70.11; 424/70.13; 424/70.19; 424/70.22; 424/70.27; 424/70.31
(58) Field of Search ............................... 424/70.1, 70.11, 424/70.13, 70.19, 70.21, 70.22, 70.27, 70.31

(56) References Cited

U.S. PATENT DOCUMENTS

| 4,031,307 | 6/1977 | DeMartino et al. |
| 4,842,849 | * 6/1989 | Grollier et al. |
| 5,476,649 | * 12/1995 | Naito et al. |
| 5,661,118 | * 8/1997 | Cauwet et al. |
| 5,685,882 | * 11/1997 | Samain et al. |

FOREIGN PATENT DOCUMENTS

| 0 291 207 | 11/1988 | (EP) . |
| 57-162797 | 10/1982 | (JP) . |
| 62-149797 | 7/1987 | (JP) . |
| 63-280008 | 11/1988 | (JP) . |
| 63-280798 | 11/1988 | (JP) . |
| 4-122797 | 4/1992 | (JP) . |
| 4-122799 | 4/1992 | (JP) . |
| 5-92914 | 4/1993 | (JP) . |
| 6-316546 | 11/1994 | (JP) . |
| 7-304652 | 11/1995 | (JP) . |
| 7-304653 | 11/1995 | (JP) . |
| 8-3101 | 1/1996 | (JP) . |
| 8-269482 | 10/1996 | (JP) . |
| 8-269487 | 10/1996 | (JP) . |
| 8-269489 | 10/1996 | (JP) . |
| 97/46211 | * 11/1997 | (WO) . |

OTHER PUBLICATIONS

Hawley's Condensed Chemical Dictionary (John Wiley & Sons, Inc. 1997).*
English language Derwent Abstract of JP 57–162797.
English language Derwent Abstract of JP 62–149797.
English language Derwent Abstract of JP 63–280008.
English language Derwent Abstract of JP 4–122797.
English language Derwent Abstract of JP 4–122799.
English language Derwent Abstract of JP 5–92914.
English language Derwent Abstract of JP 6–316546.
English language Derwent Abstract of JP 7–304653.
English language Derwent Abstract of JP 7–304652.
English language Derwent Abstract of JP 8–3101.
English language Derwent Abstract of JP 8–269487.
English language Derwent Abstract of JP 8–269589.
Chemical Abstracts, vol. 124, No. 14, Apr. 1, 1996, Abstract No. 185147.
Patent Abstracts of Japan, vol. 013, No. 105, Mar. 13, 1989 (JP 63 280008).
Patent Abstracts of Japan, vol. 017, No. 426, Aug. 9, 1993 (JP 05 092914).
Patent Abstracts of Japan, vol. 1996, No. 03, Mar. 29, 1996 (JP 07 304652).
Amihud Karmer, "Revised Tables for Determining Significance of Differences", Food Technology, vol. 17, No. 12, Dec. 1963, pp. 124–125.
M.R. Porter, "Handbook of Surfactants", Blackie & Son Ltd., Glasgow & London, 1991, pp. 116–178.
English language Derwent Abstract of JP 63–280798.
English language Derwent Abstract of JP 8–269482.

* cited by examiner

Primary Examiner—Thurman K. Page
Assistant Examiner—P. E. McQueeney
(74) Attorney, Agent, or Firm—Finnegan, Henderson, Farabow, Garrett & Dunner, LLP

(57) ABSTRACT

The invention relates to novel detergent cosmetic compositions comprising, in a cosmetically acceptable medium, at least one anionic hydroxyalkyl ether carboxylic acid surfactant and at least one cationic galactomannan gum.

27 Claims, No Drawings

DETERGENT COMPOSITIONS CONTAINING AN HYDROXYLALKYL ETHER SURFACTANT AND A CATIONIC GUAR GUM

The present invention relates to novel cosmetic compositions comprising, in a cosmetically acceptable medium, at least one anionic surfactant chosen from hydroxyalkyl ether carboxylic acid and salts thereof, and at least one cationic galactomannan gum.

It is common practice to use detergent compositions (shampoos or shower gels) based essentially on standard surfactants of anionic, nonionic and/or amphoteric type in particular, but most particularly of anionic type, to clean and/or wash the hair and/or the skin. These compositions are applied to wet hair or skin and the lather generated by massaging or rubbing with the hands removes, after rinsing with water, the various types of soiling initially present on the hair or the skin.

Admittedly, these base compositions have good washing power, but the intrinsic cosmetic properties associated with them nevertheless remain fairly poor, in particular on account of the fact that the relatively aggressive nature of such a cleaning treatment can, in the long run, lead to more or less pronounced damage to the keratin substances. This damage can be associated in particular with the gradual removal of the lipids or proteins contained in or on the surface of these substances.

Thus, in order to improve the cosmetic properties of the above detergent compositions, and more particularly of those which are intended to be applied to sensitized hair (i.e. hair which has been damaged or made brittle, in particular under the chemical action of atmospheric agents and/or hair treatments such as permanent-waving, dyeing or bleaching), it is now common practice to introduce additional cosmetic agents known as conditioners into these compositions, these conditioners being intended mainly to repair or limit the harmful or undesirable effects induced by the various treatments or aggressions to which the hair fibres are subjected more or less repeatedly. Needless to say, these conditioners may also improve the cosmetic behaviour of natural hair.

The conditioners most commonly used to date in shampoos are cationic polymers, silicones and/or silicone derivatives, which give washed, dry or wet hair an ease of disentangling, softness and smoothness which are markedly better than that which can be obtained with corresponding cleaning compositions from which they are absent.

However, despite the progress recently made in the field of shampoos based on cationic and/or silicone polymers, these shampoos are not really entirely satisfactory, such that there is currently still a strong need to be able to provide novel products which have improved performance qualities as regards one or more of the cosmetic properties mentioned above.

Anionic surfactants of hydroxyalkyl ether carboxylic acid type have already been recommended in detergent cosmetic compositions. They have been described, for example, in patent applications J63280798, J08268487 and J08269482, all of which are incorporated herein by reference.

Compositions for washing the hair using these surfactants alone do not give satisfactory cosmetic properties.

One aim of the invention is thus to propose detergent cosmetic compositions which have improved cosmetic properties, in particular in terms of disentangling, smoothness and softness of the hair. It has not been found that these aims can be achieved by combining specific cationic polymers and an anionic surfactant of hydroxyalkyl ether carboxylic acid type.

These novel compositions allow better application of these cationic polymers onto keratin substances (in particular the hair) than a composition containing standard anionic surfactants such as alkyl ether carboxylate salts, but without having a greasy look or feel.

The compositions in accordance with the invention give keratin substances, in particular the hair, a noteworthy treating effect which is manifested in particular by an ease of disentangling, as well as providing volume, lightness, smoothness, softness, suppleness and hold without any lank feel.

One subject of the invention is thus a detergent cosmetic composition, characterized in that it comprises, in a cosmetically acceptable medium, at least one cationic galactomannan gum and at least one anionic surfactant chosen from 2-hydroxyalkyl ether carboxylic acid and salts thereof.

Another subject of the invention relates to a process for treating keratin substances, such as the hair, characterized in that it consists in applying cosmetic compositions according to the invention to the said substances.

Another subject of the invention is the use of at least one anionic surfactant chosen from 2-hydroxyalkyl ether carboxylic acid and salts thereof in or for the manufacture of detergent cosmetic compositions comprising at least one cationic galactomannan gum.

According to the present invention, the expressions "keratin substances" means the hair, the eyelashes, the eyebrows, the skin, the nails, mucous membranes or the scalp, and more particularly the hair.

The various subjects of the invention will now be discussed in detail. All of the meanings and definitions of the compounds used in the present invention given below are valid for all of the subjects of the invention.

The anionic surfactants chosen from 2-hydroxyalkyl ether carboxylic acid and salts thereof, can have the following structure:

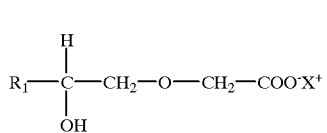

(I)

wherein $R_1$ denotes a saturated or unsaturated, linear or branched alkyl radical comprising from 8 to 30 carbon atoms; and X denotes hydrogen or an inorganic or organic cation such as: those derived from an alkali metal (for example $Na^+$ or $K^+$), $NH_4^+$, the ammoniums derived from basic amino acids, such as lysine, arginine, sarcosine, ornithine or citrulline, or from amino alcohols such as monoethanolamine, diethanolamine, triethanolamine, glucamine, N-methyl glucamine or 3-amino-1, 2-propanediol.

2-Hydroxyalkyl ether carboxylic acids or salts thereof that are preferred according to the present invention are compounds of formula (I) in which $R_1$ more particularly denotes a saturated or unsaturated, linear or branched alkyl radical comprising from 8 to 18 carbon atoms. Even more preferably, $R_1$ denotes a $C_8$–$C_{18}$ radical or a mixture of $C_8$–$C_{18}$ radicals derived from coconut oil.

Among the surfactants of formula (I), mention may be made of the product sold under the name Beaulight Shaa by the company Sanyo.

According to the invention, the anionic surfactant chosen from 2-hydroxyalkyl ether carboxylic acid and salts thereof can represent from 1% to 30% by weight, preferably from 3% to 15% by weight, relative to the total weight of the final composition.

The compositions in accordance with the invention also necessarily comprise a cationic galactomannan gum. In one embodiment, the galactomannan gum is a cationic guar gum.

The cationic galactomannan gums preferably have a cationic charge density of less than or equal to 1.5 meq/g and more particularly between 0.1 and 1 meq/g.

In general, for the purposes of the present invention, the expression "cationic galactomannan gum" means any galactomannan gum containing cationic groups and/or groups that can be ionized into cationic groups.

The preferred cationic groups are chosen from those comprising primary, secondary, tertiary and/or quaternary amine groups.

The cationic galactomannan gums used generally have a weight-average molecular mass of between approximately 500 and approximately $5 \times 10^6$, and preferably between approximately $10^3$ and approximately $3 \times 10^6$.

The cationic galactomannan gums which can be used according to the present invention are, for example, gums comprising at least one cationic tri($C_1$–$C_4$)alkylammonium group. Preferably, 2 to 30%, in numerical terms, of the hydroxyl functions in these gums bear at least one cationic trialkylammonium group. Among these trialkylammonium groups, mention may be made most particularly of trimethylammonium and triethylammonium groups. Even more preferably, these groups represent from 5 to 20% by weight relative to the total weight of the modified galactomannan gum.

In one embodiment according to the invention, a guar gum comprising at least onehydroxypropyl trimethylammonium group, i.e. a guar gum modified, for example, with 2,3-epoxypropyltrimethylammonium chloride, is used.

These galactomannan gums, in particular guar gums, modified with cationic groups are products that are already known per se and are described, for example, in U.S. Pat. Nos. 3,589,578 and 4,031,307, both of which are incorporated herein by reference. Such products are moreover sold under the trade names Jaguar C13S, Jaguar C15, Jaguar C17 and Jaguar C162 by the company Meyhall.

According to the invention, the cationic guar gum can represent from 0.001% to 10% by weight, preferably from 0.005% to 5% by weight and even more preferably from 0.01% to 3% by weight, of the total weight of the final composition.

The compositions of the invention also advantageously contain at least one other surfactant which is generally present in an amount of between 0.5% and 40% by weight approximately, preferably between 3% and 30% and even more preferably between 5% and 20%, relative to the total weight of the composition.

This surfactant can be chosen from anionic, amphoteric, nonionic and cationic surfactants, or mixtures thereof.

The additional surfactants which are suitable for carrying out the present invention are, in particular, the following:

(i) Anionic surfactant(s)

In the context of the present invention, their nature is generally not of essential importance.

Thus, as examples of anionic surfactants which can be used, alone or as mixtures, in the context of the present invention, mention may be made in particular (non-limiting list) of salts (in particular alkaline salts, especially sodium salts, ammonium salts, amine salts, amino alcohol salts or magnesium salts) of the following compounds: alkyl sulphates, alkyl ether sulphates, alkylamido ether sulphates, alkylarylpolyethersulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyl taurates, the alkyl or acyl radical of all of these various compounds preferably containing from 8 to 24 carbon atoms, and the aryl radical preferably denoting a phenyl or benzyl group. Among the anionic surfactants which can also be used, mention may also be made of fatty acid salts such as salts of oleic, ricinoleic, palmitic or stearic acid, coconut oil acid or hydrogenated coconut oil acid; acyl lactylates in which the acyl radical contains 8 to 20 carbon atoms. Mention may also be made of weakly anionic surfactants, such as alkyl D-galactosiduronic acids and their salts, as well as polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkylamido ether carboxylic acids and their salts, in particular those containing from 2 to 50 ethylene oxide groups, and mixtures thereof.

Among the anionic surfactants, it is preferred, according to the invention, to use alkyl sulphate salts and alkyl ether sulphate salts and mixtures thereof.

(ii) Nonionic surfactant(s)

The nonionic surfactants are, themselves also, compounds that are well known per se (see in particular in this respect "Handbook of Surfactants" by M. R. Porter, published by Blackie & Son (Glasgow and London), 1991, pp. 116–178) and, in the context of the present invention, their nature is generally not of essential importance. Thus, they can be chosen in particular (non-limiting list) from polyethoxylated, polypropoxylated or polyglycerolated fatty alcohols, α-diols, alkylphenols or acids having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5 and in particular 1.5 to 4 glycerol groups; polyethoxylated fatty amines preferably having 2 to 30 mol of ethylene oxide, oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable for incorporation into the context of the present invention.

(iii) Amphoteric surfactant(s)

The additional amphoteric surfactants, whose nature is generally not of essential importance in the context of the present invention, can be, in particular (non-limiting list), aliphatic secondary or tertiary amine derivatives, in which the aliphatic radical is a straight or branched chain containing 8 to 22 carbon atoms and containing at least one aqueous-solubilizing anionic group (for example carboxylate, sulphonate, sulphate, phosphate or phosphonate); mention may also be made of ($C_8$–$C_{20}$)

alkylbetaines, sulphobetaines, $(C_8-C_{20})$alkyl-amido$(C_1-C_6)$ alkylbetaines or $(C_8-C_{20})$alkylamido$(C_1-C_6)$-alkylsulphobetaines.

Among the amine derivatives, mention may be made of the products sold under the name Miranol, as described in U.S. Pat. Nos. 2,528,378 and 2,781,354, both of which are incorporated herein by reference, and having the structures:

in which $R_2$ denotes an alkyl radical derived from an acid $R_2$—COOH present in hydrolysed coconut oil, for example, a saturated or unsaturated, linear or branched $(C_5-C_{19})$alkyl radical, a heptyl radical, nonyl or undecyl radical, $R_3$ denotes a β-hydroxyethyl group and $R_4$ denotes a carboxymethyl group; and

in which B represents —$CH_2CH_2OX'$, C represents —$(CH_2)_z$—Y', with z=1 or 2, X' denotes the —$CH_2CH_2$—COOH group or a hydrogen atom, Y' denotes —COOH or the —$CH_2$—CHOH—$SO_3H$ radical, $R_5$ denotes an alkyl radical of a carboxylic acid present in coconut oil or in hydrolysed linseed oil, for example, a saturated or unsaturated, linear or branched $(C_5-C_{19})$alkyl radical, an alkyl radical, in particular, a $C_7$, $C_9$, $C_{11}$ or $C_{13}$ alkyl radical, a $C_{17}$ alkyl radical and its iso form, or an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, cocoamphodipropionic acid.

By way of example, mention may be made of cocoamphodiacetate sold under the trade name Miranol® C2M concentrate by the company Rhodia Chimie.

In the compositions in accordance with the invention, mixtures of surfactants are preferably used, and in particular mixtures of anionic surfactants and mixtures of anionic surfactants and amphoteric or nonionic surfactants. A particularly preferred mixture is a mixture consisting of at least one anionic surfactant and at least one amphoteric surfactant.

An additional anionic surfactant is preferably used which is chosen from sodium, triethanolamine or ammonium $(C_{12}-C_{14})$alkyl sulphates, sodium, triethanolamine or ammonium $(C_{12}-C_{14})$alkyl ether sulphates oxyethylenated with 2.2 mol of ethylene oxide, sodium cocoyl isethionate and sodium α-$(C_{14}-C_{16})$olefin sulphonate and mixtures thereof with:

either an amphoteric surfactant such as the amine derivatives known as disodium cocoamphodipropionate or sodium cocoamphopropionate, sold in particular by the company Rhodia Chimie under the trade name "Miranol® C2M CONC" as an aqueous solution containing 38% active material, or under the name Miranol® C32;

or an amphoteric surfactant such as alkylbetaines, in particular the cocobetaine sold under the name "Dehyton® AB30" as an aqueous solution containing 32% AM by the company Henkel, or such as $(C_8-C_{20})$ alkylamido$(C_1-C_6)$alkylbetaines, in particular Tegobetaine® F 50 sold by the company Goldschmidt.

The anionic surfactant(s) other than the 2-hydroxyalkyl ether carboxylic acid or salts thereof are generally present in a proportion of from 1 to 30% by weight, preferably from 3 to 15% by weight, relative to the total weight of the composition.

The amphoteric or nonionic surfactant(s) are generally present in a proportion of from 0.5 to about 15% by weight, preferably from 1 to 5% by weight, relative to the total weight of the composition.

The quantity and quality of the surfactants are those which are sufficient to give the final composition a satisfactory foaming power and/or satisfactory detergent power.

In the composition according to the present invention, the detergent surfactants in total generally represent from 4 to 50% by weight and preferably from 6 to 35% by weight and more particularly from 8 to 25% by weight relative to the total weight of the composition.

Cationic surfactants can also be used, among which mention may be made in particular (non-limiting list) of: optionally polyoxyalkylenated primary, secondary or tertiary fatty amine salts; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The composition of the invention can also contain at least one additive chosen from thickeners, surfactants, fragrances, nacres, preserving agents, sunscreens, anionic, nonionic or amphoteric polymers, cationic polymers other than galactomannan gums, proteins, protein hydrolysates, ceramides, pseudoceramides, fatty acids containing linear or branched $C_{16}-C_{40}$ chains, such as 18-methyl eicosanoic acid, hydroxy acids, vitamins, panthenol, silicones, plant oils, mineral oils and synthetic oils, antidandruff agents or any other additive conventionally used in cosmetics which does not affect the stability and the properties of the compositions according to the invention.

These additives are present in the composition according to the invention in proportions which can range from 0 to 50% by weight relative to the total weight of the composition. The precise amount of each additive is readily determined by a person skilled in the art on the basis of its nature and its function.

The cosmetically acceptable medium can consist solely of water or of a mixture of water and a cosmetically acceptable solvent such as a $C_1-C_4$ lower alcohol, for instance ethanol, isopropanol, tert-butanol or n-butanol; alkylene glycols such as propylene glycol, and glycol ethers.

Preferably, the composition comprises from 50 to 95% by weight of water relative to the total weight of the composition.

The detergent compositions according to the invention have a final pH generally of between 3 and 10. Preferably, this pH is between 4 and 8. Adjustment of the pH to the desired value can be carried out conventionally by adding a base (organic or inorganic) to the composition, for example aqueous ammonia or a primary, secondary or tertiary (poly) amine such as monoethanolamine, diethanolamine, triethanolamine, isopropanolamine or 1,3-propanediamine, or alternatively by adding an inorganic or organic acid, preferably a carboxylic acid such as, for example, citric acid.

In addition to the combination defined above, the compositions in accordance with the invention can contain viscosity modifiers such as electrolytes, or thickeners. Mention may be made in particular of sodium chloride, sodium xylenesulphonate, scleroglucanes, xanthan gums, fatty acid alkanolamides, alkyl ether carboxylic acid alkanolamides optionally oxyethylenated with up to 5 mol of ethylene oxide, such as the product sold under the name "Aminol A15" by the company Chem Y, crosslinked polyacrylic acids and acrylic acid/$C_{10}$–$C_{30}$ alkyl acrylate crosslinked copolymers. These viscosity modifiers are used in compositions according to the invention in proportions which can range up to 10% by weight relative to the total weight of the composition.

The compositions in accordance with the invention can also contain up to 5% of nacres or opacifiers that are well known in the prior art, such as, for example, sodium or magnesium palmitate, sodium or magnesium stearate or hydroxystearate, acyl derivatives containing a fatty chain, such as ethylene glycol or polyethylene glycol monostearate or distearate, and ethers containing a fatty chain, such as, for example, distearyl ether or 1-(hexadecyloxy)-2-octadecanol.

The compositions according to the invention can also contain foam synergists such as $C_{10}$–$C_{18}$ 1,2-alkanediols or fatty alkanolamides derived from mono- or diethanolamine.

The compositions in accordance with the invention can be used for washing and treating keratin substances such as the hair, the skin, the eyelashes, the eyebrows, the nails, the lips or the scalp, and more particularly the hair.

In particular, the detergent compositions according to the invention are shampoos, shower gels and bubble baths.

The compositions of the invention can also be in the form of rinse-out or leave-in conditioners, permanent-waving, hair-straightening, dyeing or bleaching compositions, or alternatively in the form of rinse-out compositions to be applied before or after dyeing, bleaching, permanent-waving or straightening the hair or between the two steps of a permanent-waving or hair-straightening operation.

The compositions of the invention can also be in the form of make-up-removing products.

The compositions according to the invention can be in the form of a gel, a milk, a cream, an emulsion, a thickened lotion or a mousse and can be used for the skin, the scalp, the nails, the eyelashes, the lips and more particularly the hair.

These detergent compositions are preferably foaming and the foaming power of the compositions of the invention, characterized by a foam height, is generally greater than 75 mm, preferably greater than 100 mm, measured according to the modified Ross-Miles method (NF T 73-404/ISO696).

The modifications of the method are as follows:

The measurement is carried out at a temperature of 22° C. with osmosed water. The concentration of the solution is 2 g/l. The drop height is 1 m. The amount of composition which is dropped is 200 ml. These 200 ml of composition fall into a measuring cylinder with a diameter of 50 mm and containing 50 ml of the composition to be tested. The measurement is carried out 5 minutes after stopping the flow of the composition.

A subject of the invention is also a process for treating keratin substances such as the skin or the hair, characterized in that it consists in applying a cosmetic composition as defined above to keratin substances, and then in optionally rinsing them, in particular with water.

Thus, this process according to the invention allows the treatment, care, washing of or removal of make-up from the skin, the hair or any other keratin substance.

In all the text hereinabove and hereinbelow, the percentages expressed are on a weight basis.

The invention will now be illustrated more fully with the aid of the examples which follow, which cannot be considered as limiting it to the embodiments described. In the examples, AM means active material.

EXAMPLE 1

Two shampoo compositions were prepared, one in accordance with the invention and the other (B) a comparative composition:

| | A Invention | B Comparative |
|---|---|---|
| Akyposoft 45 NV from KAO | — | 15 gAM |
| Sodium 2-(2-hydroxylauryloxy)acetate Beaulight Shaa from Sanyo | 15 gAM | — |
| Cationic guar gum (Jaguar C13 S from Meyhall) | 1 g | 1 g |
| Citric acid qs pH | 7 | 7 |
| Demineralized water qs | 100 g | 100 g | in which Akyposoft 45 NV (KAO) is sodium lauryl ether carboxylate containing 4.5 EO as an aqueous solution containing 22% active material; and Beaulight Shaa from Sanyo is sodium 2-(2-hydroxylauryloxy)acetate as an aqueous solution containing 30% active material.

A shampoo wash was carried out by applying about 1 g of composition A or composition B to locks (2.5 g) of bleached hair which has been made wet beforehand. The shampoo was worked into a lather, left to stand on the hair for 10 minutes and then rinsed out thoroughly with running water.

The disentangling of wet hair treated with these two shampoos was then compared by means of a sensory evaluation test.

The aim of the test used was to classify, by jury, each series of 2 samples, giving a grade of 1 to the lock which disentangles more easily and a grade of 2 to the lock which disentangles less easily. The 2 locks of the same series were presented simultaneously to the judge. The statistical analysis of the results was carried out using the tables by A. Kramer (Food Technology 17 --(12), 124–125 1963).

The 10 testers unanimously declared that the hair washed with composition A was significantly easier to disentangle than that treated with composition B.

What is claimed is:

1. A detergent cosmetic composition comprising at least one cationic galactomannan gum and at least one anionic surfactant chosen from 2-hydroxyalkylcarboxylic acid and salts thereof.

2. A composition according to claim 1, wherein said at least one anionic surfactant has the following structure:

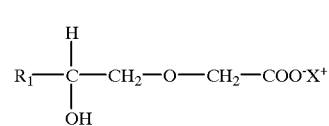

(I)

wherein $R_1$ denotes a saturated or unsaturated, linear or branched alkyl radical comprising from 8 to 30 carbon atoms; and X denotes hydrogen or an inorganic or organic cation.

3. A composition according to claim 2, wherein said radical $R_1$ denotes a saturated or unsaturated, linear or branched alkyl radical comprising from 8 to 18 carbon atoms.

4. A composition according to claim 2, wherein said radical $R_1$ is derived from coconut oil.

5. A composition according to claim 1, wherein said at least one cationic galactomannan gum comprises at least one cationic tri($C_1$–$C_4$)alkylammonium group.

6. A composition according to claim 1, wherein said at least one galactomannan gum comprises at least one trimethylammonium group.

7. A composition according to claim 1, wherein said at least one galactomannan gum is modified with at least one hydroxypropyl trimethylammonium group.

8. A composition according to claim 1, wherein said at least one cationic galactomannan gum is a cationic guar gum.

9. A composition according to claim 1 wherein said at least one anionic surfactant is present in a concentration ranging from 1 and 30% by weight relative to the total weight of the composition.

10. A composition according to claim 1 wherein said at least one anionic surfactant is present in a concentration ranging from 3 and 15% by weight relative to the total weight of the composition.

11. A composition according to claim 1, wherein said at least one cationic galactomannan gum is present in a concentration ranging from 0.001% and 10% by weight relative to the total weight of the composition.

12. A composition according to claim 1, wherein said at least one cationic galactomannan gum is present in a concentration ranging from 0.005% and 5% by weight relative to the total weight of the composition.

13. A composition according to claim 1, wherein said at least one cationic galactomannan gum is present in a concentration ranging from 0.01% and 3% by weight relative to the total weight of the composition.

14. A composition according to claim 1, further comprising at least one additional surfactant chosen from at least one anionic surfactant, at least one cationic surfactant, at least one nonionic surfactant, and at least one amphoteric surfactant.

15. A composition according to claim 14, wherein said at least one additional surfactant is present in a concentration ranging from 0.5% and 40% by weight relative to the total weight of the composition.

16. A composition according to claim 14, wherein said at least one additional surfactant is present in a concentration ranging from 3% and 30% by weight relative to the total weight of the composition.

17. A composition according to claim 14, wherein said at least one additional surfactant is present in a concentration ranging from 5% and 20% by weight relative to the total weight of the composition.

18. A composition according to claim 1, further comprising at least one additive chosen from thickeners, fragrances, nacres, preserving agents, sunscreens, cationic surfactants, anionic, nonionic or amphoteric polymers, cationic polymers other than galactomannan gums, proteins, protein hydrolysates, ceramides, pseudoceramides, a fatty acid containing linear or branched $C_{16}$–$C_{40}$ chains, hydroxy acids, vitamins, panthenol, silicones, plant oils, mineral oils and synthetic oils.

19. A composition according to claim 18, wherein said fatty acid containing linear or branched $C_{16}$–$C_{40}$ chains is chosen from 18-methyl eicosanoic acid.

20. A composition according to claim 1, wherein said composition is in a cosmetically acceptable aqueous medium.

21. A composition according to claim 1, wherein said composition is in the form of a shampoo, a shower gel, a bubble bath, a rinse-out or leave-in conditioner, a composition for permanent-waving the hair, a composition for straightening the hair, a composition for dyeing the hair, or a composition for bleaching the hair.

22. A composition according to claim 1, wherein said composition is in the form of a rinse-out composition to be applied before or after dyeing, bleaching, permanent-waving or straightening the hair, or between the two steps of a permanent-waving or hair-straightening operation.

23. A process for washing keratin substances comprising applying to said keratin substances a cosmetic composition comprising at least one cationic galactomannan gum and at least one anionic surfactant chosen from 2-hydroxyalkylcarboxylic acid or salts thereof, and rinsing said washed keratin substances.

24. A process according to claim 23, wherein said keratin substances are hair.

25. A process for treating keratin substances comprising applying to said keratin substances a cosmetic composition comprising at least one cationic galactomannan gum and at least one anionic surfactant chosen from 2-hydroxyalkylcarboxylic acid or salts thereof.

26. A process according to claim 25, wherein said keratin substances are hair.

27. A process according to claim 25, further comprising rinsing said treated keratin substances.

* * * * *

UNITED STATES PATENT AND TRADEMARK OFFICE
CERTIFICATE OF CORRECTION

PATENT NO. : 6,290,944 B1  Page 1 of 1
DATED : September 18, 2001
INVENTOR(S) : Nathalie Garnier et al.

It is certified that error appears in the above-identified patent and that said Letters Patent is hereby corrected as shown below:

<u>Title page,</u>
Item [54], in the Title,
Line 1, after "DETERGENT", insert -- COSMETIC --;
Line 2, after "CONTAINING AN", insert -- ANIONIC --; and
Line 4, after "GUAR GUM", insert -- , AND USES THEREOF --.

Signed and Sealed this

Twenty-sixth Day of March, 2002

*Attest:*

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO.    : 6,290,944 B1
DATED         : September 18, 2001
INVENTOR(S)   : Nathalie Garnier et al.

It is certified that error appears in the above-identified patent and that said Letters Patent is hereby corrected as shown below:

Column 8,
Line 39, delete "2-hydroxyalkylcarboxylic acid," and insert -- 2-hydroxyalkyl ether carboxylic acid --;

Column 10,
Lines 30 and 39, delete "2-hydroxyalkylcarboxylic acid," and insert -- 2-hydroxyalkyl ether carboxylic acid --.

Signed and Sealed this

First Day of April, 2003

JAMES E. ROGAN
*Director of the United States Patent and Trademark Office*